United States Patent
Voncken et al.

(10) Patent No.: US 10,532,172 B2
(45) Date of Patent: Jan. 14, 2020

(54) PATIENT INTERFACE DEVICES HAVING A CAVITY AREA EXPOSED TO REDUCED PRESSURE DURING USE

(71) Applicant: KONINKLIJKE PHILIPS N.V., Eindhoven (NL)

(72) Inventors: Rudolf Maria Jozef Voncken, Eindhoven (NL); Cornelis Petrus Hendriks, Eindhoven (NL); Nicolaas Petrus Willard, Valkenswaard (NL); Mareike Klee, Straelen (DE); Joyce Van Zanten, Waalre (NL); Jacob Roger Haartsen, Eindhoven (NL); Willem Potze, Geldrop (NL); Sima Asvadi, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1072 days.

(21) Appl. No.: 14/401,279

(22) PCT Filed: May 7, 2013

(86) PCT No.: PCT/IB2013/053661
§ 371 (c)(1),
(2) Date: Nov. 14, 2014

(87) PCT Pub. No.: WO2013/171624
PCT Pub. Date: Nov. 21, 2013

(65) Prior Publication Data
US 2015/0265795 A1    Sep. 24, 2015

Related U.S. Application Data

(60) Provisional application No. 61/647,605, filed on May 16, 2012.

(51) Int. Cl.
*A61M 16/06* (2006.01)

(52) U.S. Cl.
CPC .... *A61M 16/0622* (2014.02); *A61M 16/0683* (2013.01)

(58) Field of Classification Search
None
See application file for complete search history.

(56) References Cited

U.S. PATENT DOCUMENTS

| | | | | |
|---|---|---|---|---|
| 2,166,164 A | * | 7/1939 | Lehmberg | A62B 18/025 128/206.24 |
| 2,936,458 A | * | 5/1960 | Luisada | A61F 9/027 2/435 |

(Continued)

FOREIGN PATENT DOCUMENTS

| | | |
|---|---|---|
| CN | 101785894 A | 7/2010 |
| DE | 102007030446 A1 | 1/2009 |

(Continued)

*Primary Examiner* — Kathryn E Ditmer
(74) *Attorney, Agent, or Firm* — Michael W. Haas

(57) ABSTRACT

A patient interface device uses a pressure flap which extends inwardly from an outer edge of a mask of the device. The pressure flap is for contacting the skin of the patient to provide a seal or partial seal between the mask volume and the ambient surroundings. The pressure flap includes a cavity area which is exposed to a reduced pressure compared to the mask volume. This assists in keeping the pressure flap pressed against the patient's skin, and thereby maintain a large contact area. This in turn gives a reduction in local high pressure areas.

12 Claims, 4 Drawing Sheets

(56) References Cited

U.S. PATENT DOCUMENTS

| | | | | |
|---|---|---|---|---|
| 2,939,458 | A * | 6/1960 | Lundquist | A62B 18/025 128/206.24 |
| 3,330,273 | A | 7/1967 | Bennett | |
| 3,343,535 | A * | 9/1967 | Lytle | A62B 18/02 128/206.24 |
| 3,545,436 | A * | 12/1970 | Holloway | A62B 18/02 128/206.24 |
| 4,069,516 | A * | 1/1978 | Watkins, Jr. | A62B 18/08 128/206.24 |
| H397 | H * | 1/1988 | Stark | 128/206.24 |
| 4,739,755 | A * | 4/1988 | White | A62B 18/02 128/206.12 |
| 4,770,169 | A * | 9/1988 | Schmoegner | A61M 16/06 128/206.24 |
| 4,905,683 | A * | 3/1990 | Cronjaeger | A62B 18/02 128/202.22 |
| 5,343,878 | A * | 9/1994 | Scarberry | A61H 31/02 128/200.24 |
| 5,349,949 | A * | 9/1994 | Schegerin | A62B 18/08 128/201.24 |
| 5,419,318 | A * | 5/1995 | Tayebi | A41D 13/1146 128/205.27 |
| 5,540,223 | A | 7/1996 | Starr | |
| 5,655,527 | A * | 8/1997 | Scarberry | A62B 18/02 128/205.25 |
| 7,007,696 | B2 * | 3/2006 | Palkon | A61M 16/06 128/206.24 |
| 7,472,703 | B2 * | 1/2009 | Hernandez | A61M 16/06 128/206.21 |
| 7,640,933 | B1 * | 1/2010 | Ho | A61M 16/06 128/206.21 |
| 8,276,588 | B1 * | 10/2012 | Connor | A61M 16/06 128/205.25 |
| RE44,545 | E * | 10/2013 | Schegerin | A62B 18/02 128/200.24 |
| 8,573,212 | B2 | 11/2013 | Lynch | |
| 2002/0144684 | A1 | 1/2002 | Moone | |
| 2002/0029780 | A1 * | 3/2002 | Frater | A61M 16/06 128/206.24 |
| 2003/0019496 | A1 | 1/2003 | Kopacko | |
| 2007/0044797 | A1 | 3/2007 | Ho | |
| 2008/0230068 | A1 * | 9/2008 | Rudolph | A61M 16/06 128/206.28 |
| 2008/0257354 | A1 | 10/2008 | Davidson | |
| 2008/0302365 | A1 | 12/2008 | Cohen | |
| 2009/0014007 | A1 | 1/2009 | Brambilla | |
| 2009/0114230 | A1 * | 5/2009 | Hernandez | A61M 16/06 128/206.24 |
| 2009/0139525 | A1 * | 6/2009 | Schirm | A61M 16/06 128/205.25 |
| 2009/0293880 | A1 * | 12/2009 | Rutan | A61B 5/097 128/206.21 |
| 2010/0000542 | A1 | 1/2010 | Chu | |
| 2010/0006100 | A1 * | 1/2010 | Eifler | A61M 16/06 128/206.24 |
| 2010/0006101 | A1 * | 1/2010 | McAuley | A61M 16/06 128/206.24 |
| 2010/0258131 | A1 * | 10/2010 | Gaffney | A62B 18/08 128/206.24 |
| 2011/0005524 | A1 * | 1/2011 | Veliss | A61M 16/0666 128/206.24 |
| 2011/0023882 | A1 * | 2/2011 | Nickol | A61M 16/06 128/206.24 |
| 2011/0088699 | A1 * | 4/2011 | Skipper | A61M 16/06 128/206.26 |
| 2011/0162654 | A1 * | 7/2011 | Carroll | A61M 16/06 128/206.21 |
| 2011/0174310 | A1 * | 7/2011 | Burz | B29C 45/4407 128/206.24 |
| 2011/0186051 | A1 | 8/2011 | McAuley | |
| 2011/0209701 | A1 * | 9/2011 | Derringer | A61M 16/06 128/202.17 |
| 2011/0247625 | A1 | 10/2011 | Boussignac | |
| 2012/0067349 | A1 * | 3/2012 | Barlow | A61M 16/06 128/205.25 |
| 2012/0132208 | A1 * | 5/2012 | Judson | A61M 16/0622 128/205.25 |
| 2012/0180795 | A1 * | 7/2012 | Knight | A41D 13/0556 128/206.24 |
| 2012/0204881 | A1 * | 8/2012 | Davidson | A61M 16/06 128/206.25 |
| 2013/0192601 | A1 * | 8/2013 | Reischl | A61M 16/06 128/205.25 |
| 2014/0251338 | A1 * | 9/2014 | Asvadi | A61M 16/06 128/206.22 |

FOREIGN PATENT DOCUMENTS

| | | | |
|---|---|---|---|
| DE | 102009038655 A1 | 2/2011 | |
| EP | 0788805 A2 | 8/1997 | |
| JP | 2010512193 A | 4/2010 | |
| RU | 2392010 C1 | 6/2010 | |
| WO | WO-2010139014 A1 * | 12/2010 | ............ A61M 16/06 |
| WO | WO2010148453 A1 | 12/2010 | |
| WO | WO 2011121525 A1 * | 10/2011 | ............ A61M 16/06 |

* cited by examiner

PATIENT INTERFACE DEVICES HAVING A CAVITY AREA EXPOSED TO REDUCED PRESSURE DURING USE

CROSS-REFERENCE TO RELATED APPLICATIONS

This patent application claims the priority benefit under 35 U.S.C. § 371 of international patent application no. PCT/IB2013/053661, filed May 7, 2013, which claims the priority benefit under 35 U.S.C. § 119(e) of U.S. Provisional Application No. 61/647,605 filed on May 16, 2012, the contents of which are herein incorporated by reference.

FIELD OF THE INVENTION

The present invention relates to patient interfaces for transporting a gas to and/or from an airway of a user.

BACKGROUND OF THE INVENTION

There are numerous situations where it is necessary or desirable to deliver a flow of breathing gas non-invasively to the airway of a patient, i.e. without inserting a tube into the airway of the patient or surgically inserting a tracheal tube in their oesophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnoea syndrome, in particular, obstructive sleep apnoea (OSA).

Non-invasive ventilation and pressure support therapies involve the placement of a patient interface device including a mask component on the face of a patient. The mask component may be, without limitation, a nasal mask that covers the patient's nose, a nasal pillow/cushion having nasal prongs that are received within the patient's nostrils, a nasal/oral mask that covers the nose and mouth, or a full face mask that covers the patient's face. The patient interface device interfaces between the ventilator or pressure support device and the airway of the patient, so that a flow of breathing gas can be delivered from the pressure/flow generating device to the airway of the patient.

Such devices are typically maintained on the face of a patient by headgear having one or more straps adapted to fit over/around the patient's head.

FIG. 1 shows a typical system to provide respiratory therapy to a patient. This system will be referred to in the description and claims as a "patient interface assembly".

The system 2 includes a pressure generating device 4, a delivery conduit 16 coupled to an elbow connector 18, and a patient interface device 10. The pressure generating device 4 is structured to generate a flow of breathing gas and may include, without limitation, ventilators, constant pressure support devices (such as a continuous positive airway pressure device, or CPAP device), variable pressure devices, and auto-titration pressure support devices.

Delivery conduit 16 communicates the flow of breathing gas from pressure generating device 4 to patient interface device 10 through the elbow connector 18. The delivery conduit 16, elbow connector 18 and patient interface device 10 are often collectively referred to as a patient circuit.

The patient interface device includes a mask 12 in the form of a shell 15 and cushion 14, which in the exemplary embodiment is nasal and oral mask. However, any type of mask, such as a nasal-only mask, a nasal pillow/cushion or a full face mask, which facilitates the delivery of the flow of breathing gas to the airway of a patient, may be used as mask. The cushion 14 is made of a soft, flexible material, such as, without limitation, silicone, an appropriately soft thermoplastic elastomer, a closed cell foam, or any combination of such materials.

An opening in the shell 15, to which elbow connector 18 is coupled, allows the flow of breathing gas from pressure generating device 4 to be communicated to an interior space defined by the shell 15 and cushion 14, and then to the airway of a patient.

The patient interface assembly 10 also includes a headgear component 19, which in the illustrated embodiment is a two-point headgear. Headgear component 19 includes a first and a second strap 20, each of which is structured to be positioned on the side of the face of the patient above the patient's ear.

Headgear component 19 further includes a first and a second mask attachment element 22 to couple the end of one of the straps 20 to the respective side of mask 12.

A problem with this type, of assembly is that the headgear force vectors necessary to achieve a robust and stable seal against the face of the patient can cut a straight line near the corners of a patient's eyes, which can be uncomfortable and distracting.

One design of interface between the mask cushion and the patient is a seal flap. This provides a large contact area with the skin, and it is pressed against the patient by the pressure inside the mask volume.

However, locally high pressure areas can still result around the mask part, for example resulting from a reduced contact area if there is lifting of parts of the seal flap away from the contact with the skin.

SUMMARY OF THE INVENTION

According to the invention, there is provided a device.

In one aspect, the invention provides a patient interface device comprising:

a mask for delivering a gas to the nose and/or mouth of a patient, wherein the mask comprises cushion;

wherein the cushion has a pressure flap which extends inwardly from an outer edge of the mask, wherein the pressure flap is for contacting the skin of the patient to provide a seal or partial seal between the mask volume and the ambient surroundings, wherein the pressure flap comprises a cavity area adapted to be adjacent the skin of the patient and between the mask volume and the skin of the patient, wherein the cavity area is exposed to a reduced pressure compared to the mask volume.

This design uses a pressure flap having a cavity area between the patient's skin and the mask volume. By providing a relative low pressure in this cavity (compared to the mask volume), the pressure flap is pressed against the skin over its full area, thereby reducing local areas of high pressure.

The mask can be for covering only the mouth, only the nose, the nose and mouth or even the full face.

The pressure flap can comprise a cover layer over the cavity area which comprises an inner lip which defines an inner boundary of the cavity area. This means the main seal area is made at the inner side of the pressure flap. This means lifting of the inner edge is prevented, and the low pressure cavity ensures the rest of the pressure flap is urged against the patient' skin.

The pressure flap can comprise a sealing flap and the cover layer is then an air tight layer. This provides a seal between the mask volume and the surroundings. Alternatively, the cover layer can be partially porous to allow gas flow from the mask volume to the cavity area. This provides a small air flow across the skin where contact is made and this can improve comfort.

The cavity area can be exposed to the pressure of the ambient surroundings. This provides a way of improving the seal performance in a passive way.

The cavity area can comprise a porous layer. This enables the ambient pressure to be present throughout the layer.

The cavity can comprise support structures to prevent the cavity area from collapse, under the pressure in the mask volume.

A strap arrangement is preferably provided for holding the mask against the head of the patient.

Another aspect of the invention provides a cushion for a patent interface device, wherein the cushion has a pressure flap which is arranged to extend inwardly from an outer edge of the mask, wherein the pressure flap is for contacting the skin of the patient to provide a seal or partial seal between the mask volume and the ambient surroundings, wherein the pressure flap comprises a cavity area adapted to be adjacent the skin (58) of the patient and between the mask volume and the skin of the patient, wherein the cavity area is exposed to a reduced pressure compared to the mask volume.

This cushion design can be applied to an existing patient interface design, to provide the advantages above. Thus, the invention can be embodied in a replacement cushion. By volume enclosed by the cushion is meant the space inside the cushion periphery where it is designed to contact the face. The cushion itself is not closed, and the volume is only closed when the cushion is attached to the remainder of a patient interface device.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a patient interface device uses a pressure flap which extends inwardly from an outer edge of a mask of the device. The pressure flap is for contacting the skin of the patient to provide a seal or partial seal between the mask volume and the ambient surroundings. The pressure flap comprises cavity area which is exposed to a reduced pressure compared to the mask volume. This assists in keeping the pressure flap pressed against the patient's skin, and thereby maintain a large contact area. This in turn gives a reduction in local high pressure areas.

Figure 2:
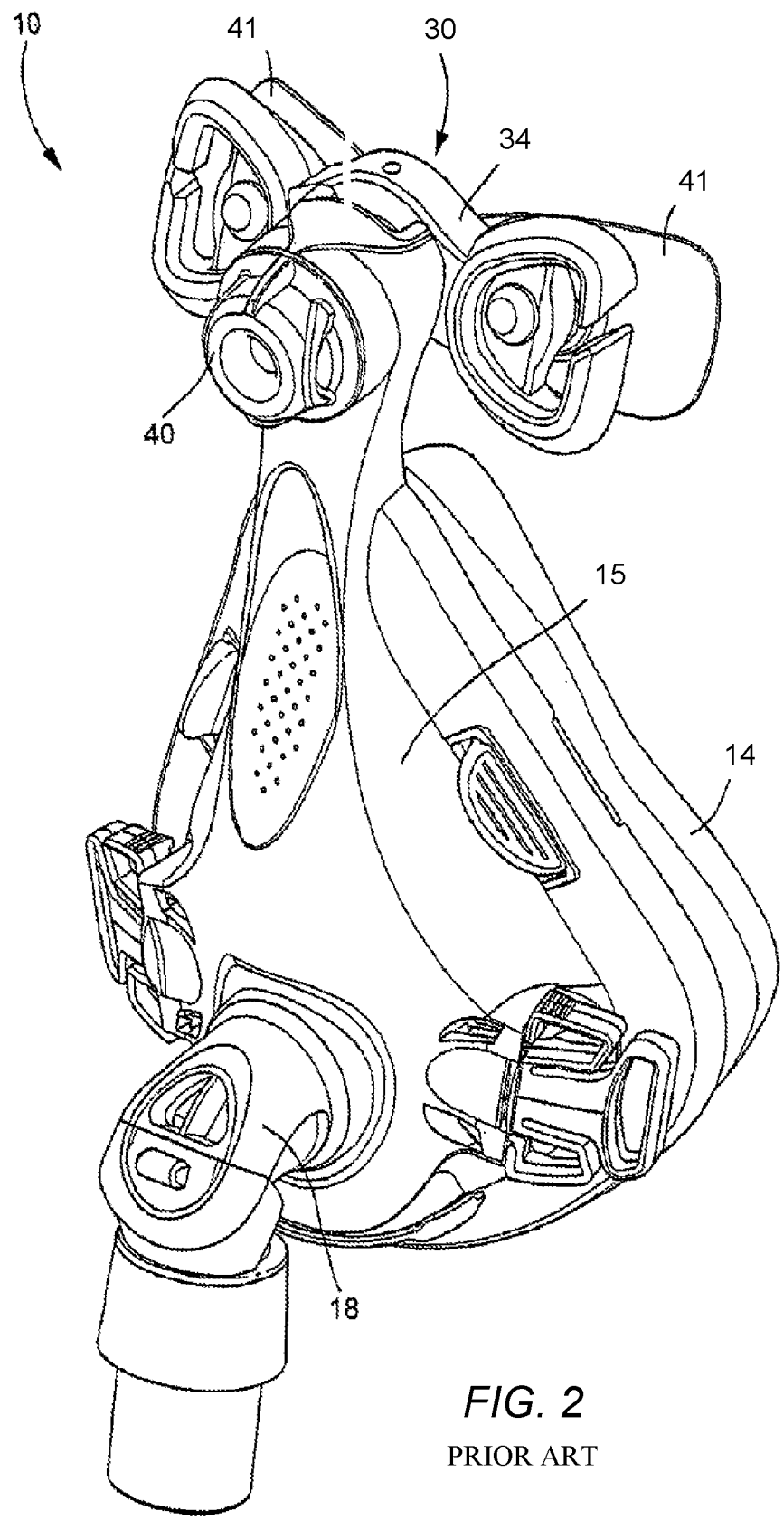
FIG. 2 shows a known patient interface as disclosed in US2010/0000542.

FIG. 2 is taken from US20100000542 and shows a patient interface arrangement in the form of a full facial mask assembly 10 including a forehead support 30.

Figure 1:
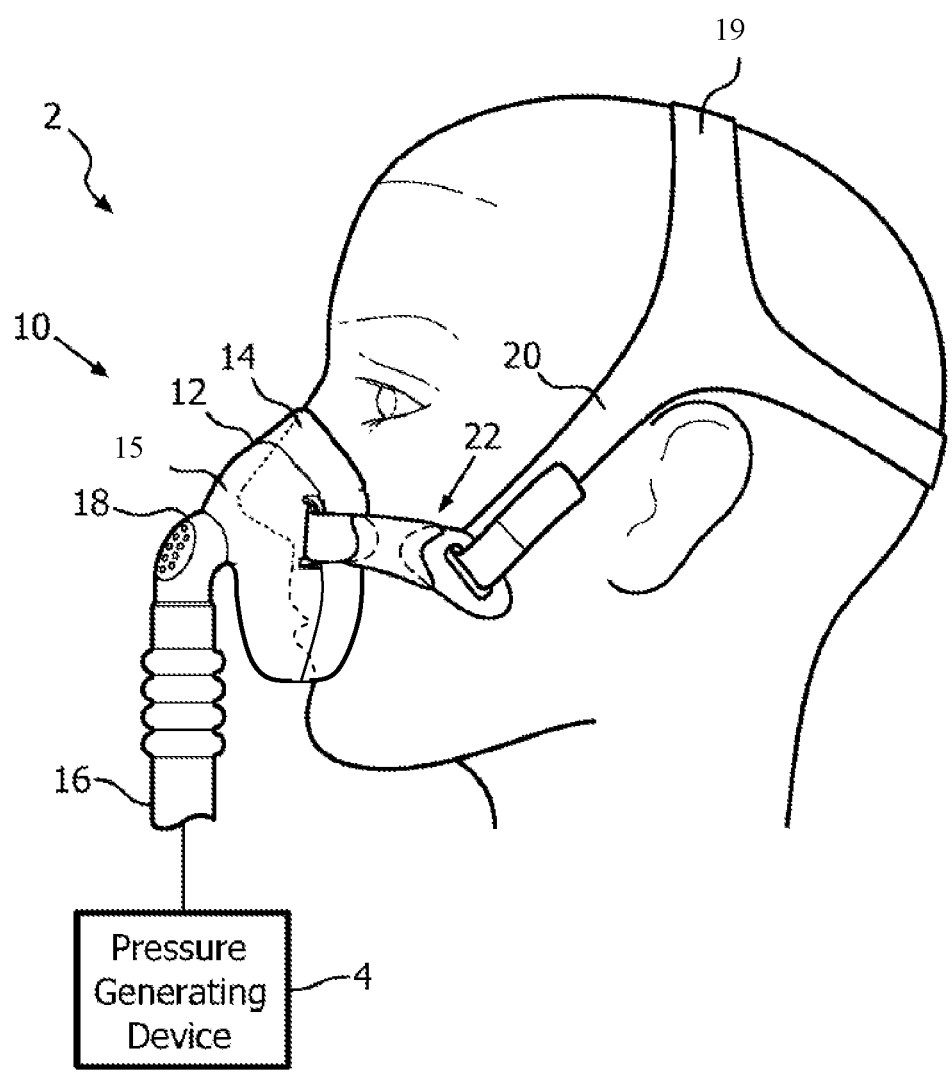
FIG. 1 shows a known patient interface.

The patient interface device (the mask part) is for delivering gas to the user and includes a shell 15, a cushion 14 adapted to form a seal with the patient's face, an elbow assembly 18 for connection to an air delivery tube (components 10,14,16,18 corresponding to those of the same number in FIG. 1).

FIG. 2 also shows a forehead support 30 for reducing the forces on the patient's face, and including a frame 34 which carries forehead support cushions 41. In this example, the position of the forehead support is adjustable by a rotary knob 40.

The forehead support aims to increase the contact area so that pressure against the skin can be reduced. However, the contact between the mask and the skin can still result in red mark formation in some form after wearing the mask for a long time. These red marks can last for minutes to several hours. Prolonged use can even to lead to pressure ulcers if the mask is put on too tightly.

The invention relates to the design of the seal part of the mask cushion.

Figure 3:
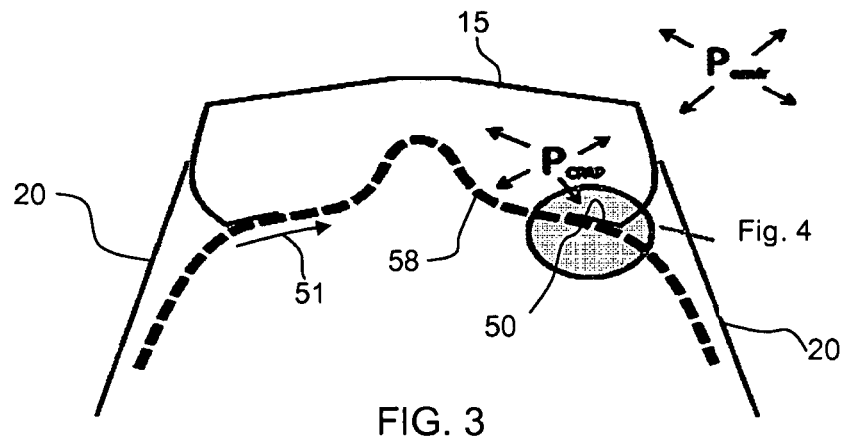
FIG. 3 shows a first example of device of the invention.

FIG. 3 shows a first example of design in accordance with the invention. The same reference numerals are used as in FIGS. 1 and 2.

The patient interface device has a mask with a shell 15 and a cushion 14. The straps 20 are also shown in FIG. 3. The invention relates to the cushion design as well as to the patient interface device as a whole.

The surface of the cushion in contact with the patient has a pressure flap 50.

In the first example, this pressure flap is a sealing flap, i.e. it includes an air tight membrane to provide a seal between the inner mask volume and the ambient surroundings. As discussed below, the pressure flap may in other examples be deliberately gas permeable to a limited extent. Thus, the term "pressure flap" is used to denote a structure to be pressed against the skin to provide a partial or complete seal.

The sealing flap extends inwardly from an outer edge of the mask in contact with the skin of the patient. By inwardly is meant in a direction towards the middle of the mask, but along the surface of the patients skin (i.e. towards the middle of the mask shape as projected from in front onto the patient's face). This inward direction is represented by arrow 51 in FIG. 3.

The pressure flap 50 is to be pressed against the user's skin to provide a large contact area and to provide a seal between the mask volume and the ambient surroundings.

Figure 4:
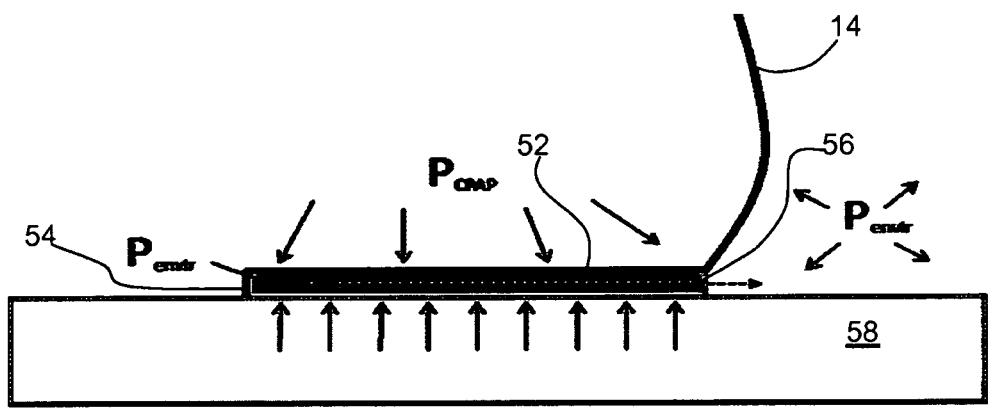
FIG. 4 shows the seal part of FIG. 3 in more detail.

FIG. 4 shows a close up of the sealing flap area. The pressure flap 50 comprises a gas tight layer 52 over a cavity area 56. The gas tight layer comprises an inner lip 54 which defines an inner boundary of the cavity area 56 and the cavity area is exposed to a reduced pressure compared to the mask volume.

The cavity can have a height in the range 2 mm to 20 mm, and the radial length of the sealing flap is typically in the range 10 mm to 40 mm.

In the example shown in FIG. 4, the cavity is exposed to the ambient pressure Penvir. This can be achieved by having the cavity filled with a porous material.

This design gives a sort of self-attaching of the pressure flap 50 to the skin 58. By maintaining a large contact area, the occurrence of locally high contact pressures is reduced and therefore the occurrence of red mark formation can be prevented. The improved contact can also enable the force required to press the seal against the face to be reduced, thereby reducing the occurrence of pressure spots.

FIG. 5 is used to explain this self-attaching function.

Figure 5A:
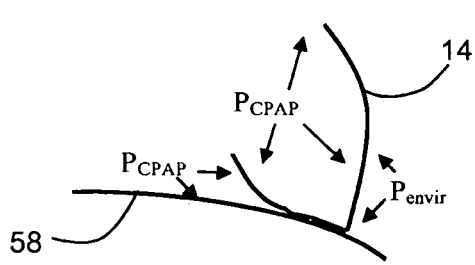
FIG. 5 is used to show how the arrangement of FIG. 4 provides improved sealing.

FIG. 5(a) shows a conventional design. A seal is intended to be made between the mask cushion 14 and the skin 58, all along the sealing flap. However, if the inner side of the flap lifts, it is in equilibrium since the internal mask pressure $P_{CPAP}$ is on both sides of the flap. The flap will only be pushed against the skin by its own elastic restoring force. However, a very elastic material is undesirable since it does not follow the skin contours well. The end result is that the main seal is around the outer edge, and this provides a smaller contact area and therefore higher pressure.

As a result of the stiffness of the mask shell and cushion 14, and the mask being pushed against the face through the mask shell and cushion, high pressure spots can result.

Figure 5B:
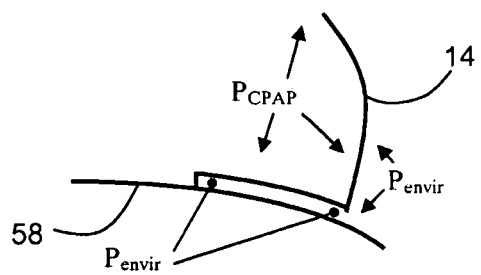

FIG. 5(b) shows how the arrangement of the invention functions. There is a seal at the inside edge of the sealing flap. Beneath this inside edge is the atmospheric pressure. As a result, if the inside edge tends to lift, there is a biasing force which urges it back down. Thus, a seal is maintained along the inner edge.

The full length (length in this case being in the inward-outward radial direction) of the sealing flap along to the outer edge is biased downwardly by the pressure difference between the mask volume and the atmospheric pressure. As a result, the full area of the sealing flap is urged against the skin to provide a large contact area and reduce localised increases in pressure.

In this way, a form of self-attachment of the sealing flap is realized by ensuring a lower air pressure in the sealing cavity than in the mask which results in the sealing flap being pushed onto the skin by the pressure difference.

In turn, this means a lower force may be needed to be applied to the mask. The mask cushion 14 can be made much more flexible since the need to push the seal to the skin is reduced.

The sealing flap design provides pressure equalization with the environmental pressure. By way of example, a spacer fabric, channel structure or material with a rough texture can be used. Essentially, these are all porous materials in that air channels extend within the cavity. These porous materials allow the inside air pressure to be equalized with the environmental air pressure by an open connection to the environment.

At the mask side, the porous material is made impermeable to air, for instance by a coating. Thus, a gas tight layer can be defined as a coating or a separately formed layer. At the environmental side, the gas tight layer is open such that the inside pressure will be equal to the environmental pressure. Due to friction between the sealing flap and the skin, frictional forces will act which will limit the amount of slipping of the sealing along the skin.

The sealing flap should be made flexible enough to adapt to the face contour smoothly and in a natural way. Furthermore, the stability of the contact with the skin will depend heavily on the contact area which is pressed onto the skin by the pressure difference. Therefore the area of the sealing flap should be designed as large as possible within other limitations, such as available face surface area and comfort.

Figure 6:
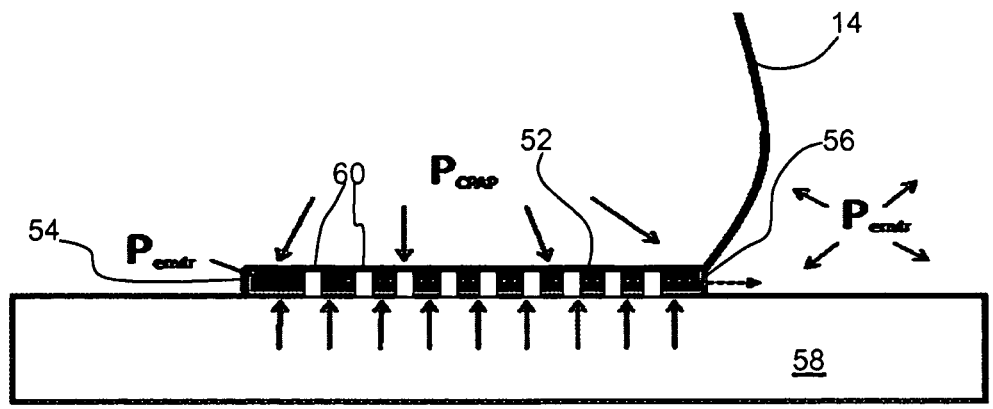
FIG. 6 shows a second example of device of the invention.

FIG. 6 shows a modification in which the sealing flap cavity has support struts 60 to prevent collapse. This is to make sure the porous channels reach the full way along the sealing flap and do not become blocked.

In the examples above, the lower pressure is achieved in a passive way. It could instead be realized in an active way by creating an under-pressure e.g. by pumping. For example, the connection between the porous cavity material and the environment can also be closed and an under-pressure in the sealing cavity can be created by active pumping.

In another possible embodiment, the pressure flap is not completely impermeable to air at the mask side but allows for a small airflow from the inside of the mask through the porous sealing cavity. Thus, a semi-permeable cover layer can provide the interface between the mask volume and the cavity area. In this case, the pressure flap performs only a partial sealing function. Alternatively, no cover layer is needed at all, and the material of cavity area simply terminates to define the interface to the mask volume. In this case, there will be a pressure gradient through the material of the cavity area and the mask volume, between the ambient pressure and the mask pressure. However, the pressure in the cavity area will again on average be lower, to provide the same sealing advantages explained above.

To enable the lower ambient pressure to extend fully into the cavity, the thickness of the cavity may need to be relatively large, for example at least one quarter or one half of the radial dimension. This prevents that the main pressure drop is restricted to the radial outer edge and thereby maintains a pressure drop in the thickness direction along the full (radial) length of the cavity.

This airflow will refresh the air inside the porous material of the cavity area which will improve the comfort of the mask by controlling the temperature and moisture level. The cover layer nevertheless presents a sufficiently large restriction to airflow at the mask side to ensure that the air pressure in the open-structure material remains (almost) equal to the environmental pressure.

Figure 7:
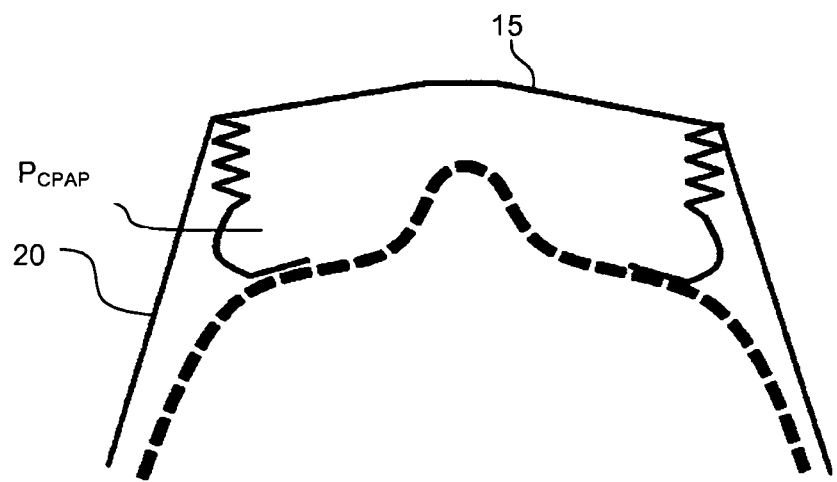
FIG. 7 shows a third example of device of the invention.

The improved seal contact can enable a reduction in the strap tightness, although of course the straps are required to hold the mask. Pressure spots on the face contact areas can be further avoided by giving the mask a low stiffness in the direction normal to the face. FIG. 7 shows schematically an example of this, in which a low stiffness area is represented by a corrugated structure.

It is known to include a forehead support to spread the required forces to hold the mask over a larger area. In this way, an additional cushion support on the forehead balances the forces put by the mask around the nose or nose and mouth. The invention can be applied to a patient interface assembly with or without a forehead support.

An example has been shown with a regular array of struts to provide support for the cavity area. These struts, or indeed other additional structures, can also be designed to create a desired pressure profile in the cavity area, for example to ensure that the ambient pressure reaches the full depth of the cavity area so that the pressure difference advantages are obtained across the full cavity area. These structures may defined passageways of varying cross section in different parts of the cavity.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A cushion for a patient interface device that includes a mask and a mask volume defined by the mask and the cushion, the cushion comprising:
a pressure flap configured to extend inwardly from an outer edge of the mask,
wherein the pressure flap comprises a cover layer configured to extend inwardly from the outer edge of the mask and between the mask volume and a skin of a patient during use, and an inner lip which extends from the cover layer generally perpendicular to the cover layer,
wherein the inner lip is disposed at an innermost edge of the pressure flap,
wherein, the inner lip is positioned and structured such that when the inner lip is disposed against the skin of the patient, a cavity area is formed which is bounded by the cover layer, the inner lip, and the skin of the patient,
wherein the inner lip is structured to provide a seal between the mask volume and the cavity area when the cushion is disposed on the patient, and
wherein the cavity area is adapted to be exposed to a pressure of an ambient surrounding outside of the cushion during use.

2. A cushion as claimed in claim 1, wherein the pressure flap comprises a sealing flap and the cover layer is an air tight layer.

3. A cushion as claimed in claim 1, wherein the cover layer is partially porous to allow gas flow from the mask volume to the cavity area.

4. A cushion as claimed in claim 1, wherein the cavity area comprises a porous layer.

5. A cushion as claimed in claim 1, wherein the cavity area comprises support structures to prevent the cavity area from collapse.

6. The cushion of claim 1, wherein the inner lip is configured to define an opening into the mask volume that is structured to receive a portion of the face of the patient and wherein the inner lip extends continuously around the opening.

7. A patient interface device comprising:
a mask defining a mask volume; and
a cushion coupled to the mask, the cushion comprising a pressure flap extending inwardly from an outer edge of the mask,
wherein the pressure flap comprises a cavity area adapted to be disposed directly against a skin of a patient and between the mask volume and the skin of the patient,
wherein the pressure flap comprises a cover layer over the cavity area and an inner lip which defines an inner boundary of the cavity area,
wherein the inner lip is positioned at an innermost portion of the pressure flap,
wherein the inner lip is positioned and structured to provide a seal between the mask volume and the cavity area when the cushion is disposed on the patient during use, and
wherein the cavity area is adapted to be exposed to a pressure of an ambient surrounding of the cushion during use.

8. A device as claimed in claim 7, wherein the cavity area comprises a porous layer.

9. A device as claimed in claim 7, wherein the cavity comprises support structures to prevent the cavity area from collapse.

10. A device as claimed in claim 7, further comprising a strap arrangement adapted to hold the mask against a head of a patient.

11. A device as claimed in claim 7, wherein the inner lip extends generally perpendicular to the cover layer and away from the mask volume.

12. A device as claimed in claim 7, wherein the inner lip defines an opening into the mask volume that is structured to receive a portion of the face of the patient and wherein the inner lip extends continuously around the opening.

* * * * *